United States Patent
Rajca

(12) 
(10) Patent No.: US 6,515,144 B2
(45) Date of Patent: Feb. 4, 2003

(54) OLIGOTHIOPHENES AND SYNTHESIS THEREOF

(75) Inventor: Andrzej Rajca, Lincoln, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 28 days.

(21) Appl. No.: 09/862,679

(22) Filed: May 22, 2001

(65) Prior Publication Data

US 2002/0193611 A1 Dec. 19, 2002

(51) Int. Cl.$^7$ .............................................. C07D 409/02
(52) U.S. Cl. ............................................ 549/41; 549/43
(58) Field of Search ....................................... 549/41, 43

(56) References Cited

U.S. PATENT DOCUMENTS

| | | | |
|---|---|---|---|
| 4,569,734 A | | 2/1986 | Naarmann et al. |
| 4,640,479 A | | 2/1987 | Shely et al. |
| 4,758,634 A | | 7/1988 | Jenekhe |
| 4,818,646 A | | 4/1989 | Takakubo et al. |
| 4,987,042 A | | 1/1991 | Jonas et al. |
| 5,108,573 A | | 4/1992 | Rubinstein et al. |
| 5,519,147 A | * | 5/1996 | Swager et al. ................ 549/59 |
| 5,919,951 A | | 7/1999 | Chmii et al. |
| 6,184,540 B1 | | 2/2001 | Chmii et al. |
| 6,242,561 B1 | * | 6/2001 | Mohwald et al. ........... 528/377 |
| 6,403,809 B1 | * | 6/2002 | Holmes et al. ............... 549/41 |

OTHER PUBLICATIONS

Gronovitz, Halogen–Metal Interconversion with Dibromobithienyls, *Acta Chem. Scand.*, 1961,\pp. 1393–1395, vol. 15, No. 6. Chemical Societies in Denmark, Finland, Norway and Sweden.

Jong et al., The Synthesis, Oxidation, and Electronic Spectra of Four Dithienothiphenes, *J. Org. Chem.*, 1971, pp. 1645–1648, vol. 36, No. 12, American Chemical Society, USA.

Kanatzidis, Conductive Polymers, *Chemical & Engineering News*, Dec. 3, 1990, pp. 36–54.

Meurer et al. Helical Molecules in Organic Chemistry, *Top Curr. Chem.*, 1985, pp. 1–76.

Navaza et al., General Models for Helicenes, *Bull. Soc. Chim. Belg.*, 1979, pp. 863–870, vol. 88, No. 11.

Suffert, Simple Direct Titration of Organolithium Reagents Using N–Pivaloyl–o–toluidine and/or N–pivaloyl–o–benzylaniline, J. *Org. Chem.*, 1989, pp. 509–510, vol. 54, No. 2, Amer. Chem. Society, USA.

* cited by examiner

*Primary Examiner*—Deborah C. Lambkin
(74) *Attorney, Agent, or Firm*—Senniger, Powers, Leavitt & Roedel

(57) ABSTRACT

Novel oligothiophenes and intermediates therefor are disclosed together with a process for synthesizing them. The oligothiophenes are in the form of a helix which contains five-membered rings unsaturated heterocycles that are cross-conjugated and annelated into a helix.

15 Claims, No Drawings

OLIGOTHIOPHENES AND SYNTHESIS THEREOF

BACKGROUND OF THE INVENTION

This invention relates to novel oligothiophenes and processes for the synthesis thereof, and more particularly, to such oligothiophenes in which the thiophene rings are cross-conjugated and annelated into a helix.

Five-membered ring unsaturated heterocycles, containing two double bonds and one heteroatom, are building blocks for conductive polymers. Polypyrrole and polythiophene are among the well-known conductive polymers with good stability and processability. These heterocycle polymers contain a pi- conjugated system (single and double bonds alternating) along a main polymer chain, linear or branched.

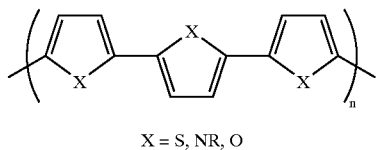

X = S, NR, O

Pi-conjugated compounds, particularly thiophene-containing or furan-containing compounds, are used in various industrial applications. For example, they can be used as dyes or pigments, as (semi)conductors, (electro) luminescent material or in optical and electro-optical devices such as light emitting diodes, field-effect transistors, solar cells, polarizing optical elements and rechargeable batteries, and electrolytic capacitors. General background concerning the structure, properties and uses of redox active, electroactive, conductive polymers is described in an article entitled "Conductive Polymers" by Mercouri G. Kanatzidis published in Chemical and Engineering News, Dec. 3, 1990 and in U.S. Pat. Nos. 4,569,734; 4,640,749; 4,818,646; 4,987,042; 5,108,573; 4,758,634; 5,919,951; and 6,184,540, each of which is incorporated herein by reference.

There remains a need for improved oligothiophenes and processes for synthesizing them.

SUMMARY OF THE INVENTION

Among the several objects of the invention may be noted the provision of novel oligothiophenes and intermediates therefor; the provision of novel processes for preparing such oligothiophenes; the provision of such processes which produce oligothiophenes in the form of a helix; and the provision of such oligothiophenes which are produced by cross-conjugating and annelating thiophene rings into a helix. Other objects and features will be in part apprent and in part pointed out hereinafter.

Briefly, the present invention is directed to compounds of the formula:

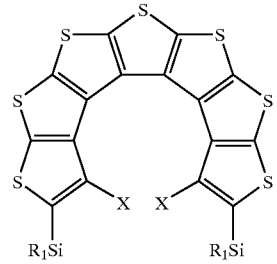

(1)

wherein X is Br or I and $R_1$ is trialkyl with the alkyl group having from 1 to 6 carbon atoms.

The invention is also directed to intermediate compounds of the formula:

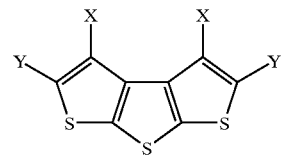

wherein X is Br or I and Y is H or $SiR_1$ wherein $R_1$ is trialkyl with the alkyl group having from 1 to 6 carbon atoms.

The invention is further directed to a process for preparing compounds of the first formula above comprising the steps of (a) converting a compound of the formula:

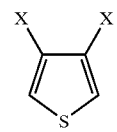

wherein X is Br or I, to a compound of the formula:

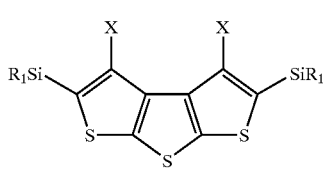

(3)

wherein X is as defined above and $R_1$ is trialkyl with the alkyl group having from 1 to 6 carbon atoms;

(b) cross-conjugating compounds of the formula (3) above to a compound of the formula:

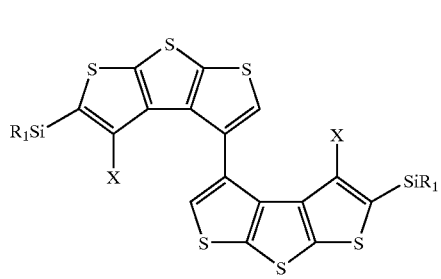

(4)

wherein X and $R_1$ are as defined above; and (c) annelating a compound of the formula (4) above to produce an oligothiophene helix of the first formula above.

DESCRIPTION OF THE PREFERRED EMBODIMENTS

In accordance with the present invention, it has now been found that novel oligothiophenes or polythiophenes of the helix formula:

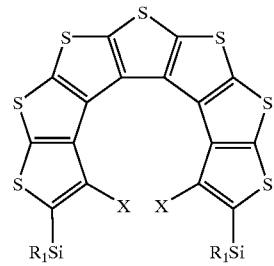

wherein X is Br or I and $R_1$ is trialkyl with the alkyl group having from 1 to 6 carbon atoms, may be synthesized by the following scheme in which five-membered thiophene heterocycles are cross-conjugated and annelated into a

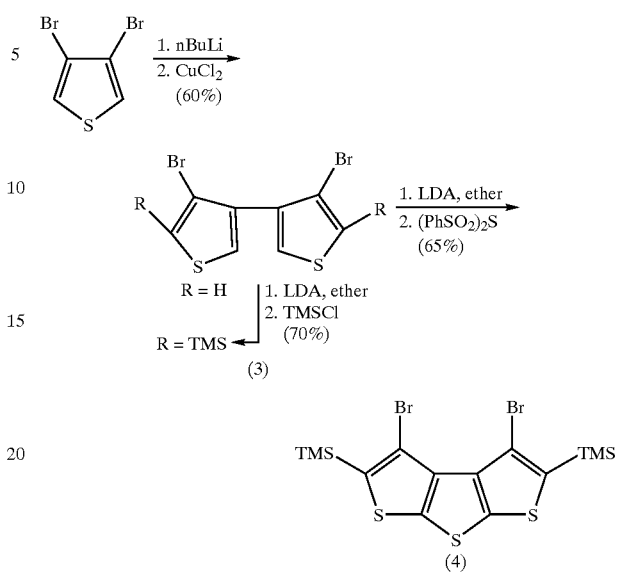

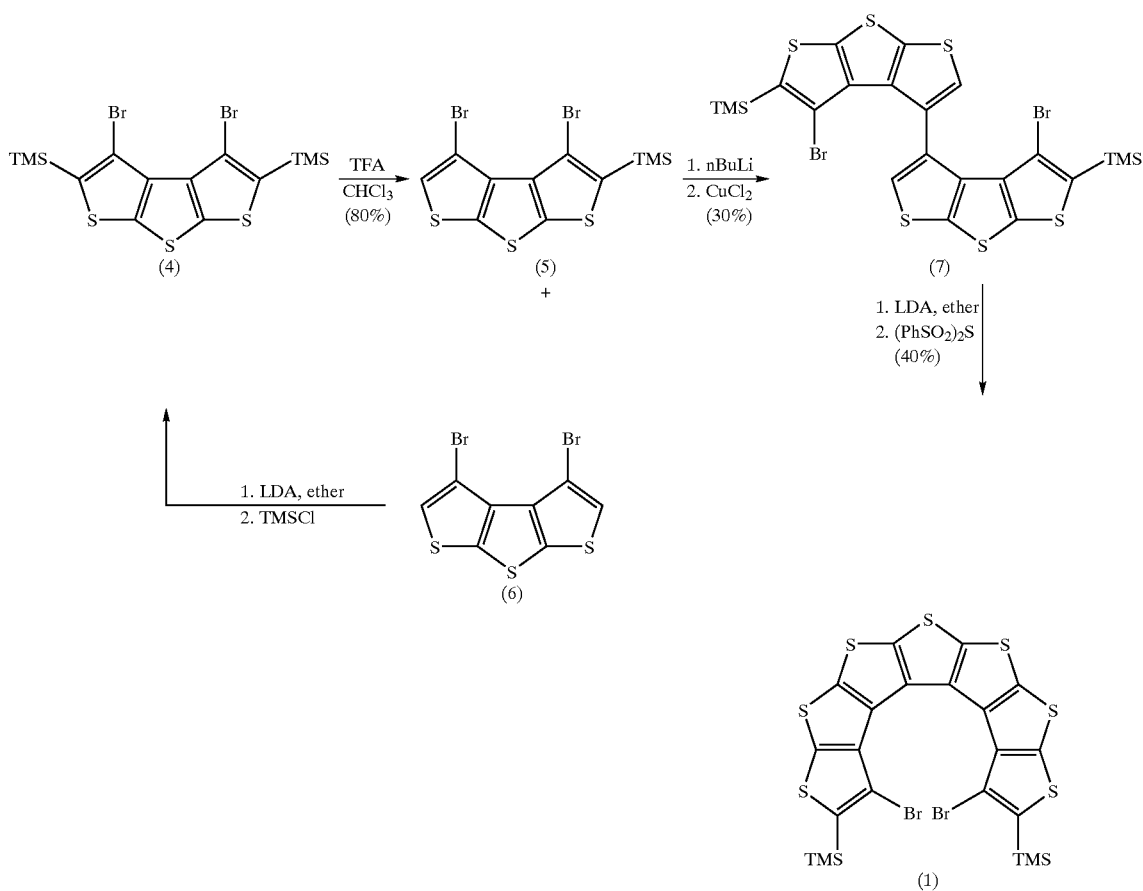

LDA=Lithium duisopropylamide: TMS=trimethylsilyl; TFA=trifluoroacetic acid.

The above synthetic route to compounds of the formula (1) consists of two iterations using 3,4-dibromo-thiophene and 4,4'-dibromo-5,5'-di(tnimethylsilyl)dithieno[2,3-b:3',2'-]thiophene (4) as the tetrafunctionalized starting modules for the first and second iterations, respectively. In each iteration, the modules are connected and then annelated. As the chirality is introduced only in the final annelation step, the stereochemical problems of racemic synthesis are avoided.

In the first iteration, 4,4'-dibromo-3,3'-bithienyl (2) is prepared from 3,4-dibromothiophene by a mono Li/Br exchange as previously reported (Gronovitz, Acta Chem Scand. 1961, 15, 1393–1395). The two most acidic a-positions in 2 are TMS-protected to give 3. Following the LDA-mediated lithiation of the unprotected a-positions in 3, the reaction of the dilithiated 3 with bis(phenylsulfonyl) sulfide gives the annelated product 4.

In the second iteration, mono Li/Br exchange in 4 is not successful. Therefore, one of the TMS groups in 4 is removed to give 5 in which a modest selectivity for the mono Li/Br exchange can be attained. The incomplete conversion of 4 into a mixture of 5 and 6 can be monitored by thin layer chromatography and NMR spectroscopy; after recycling (6 to 4 and then to 5) 5 is obtained in 80% yield. Following the single Li/Br exchange on 5, the resultant aryllithium species is oxidized with $CuCl_2$ to give 7 which is subsequently annelated to give 1.

The structures of 4 and 1 were confirmed by single-crystal X-ray analysis. In 4, all the thiophene rings are approximately coplanar. The C-Br bonds are nearly parallel, with the C2. . . C7 distance of 3.68 Å and the Br1-C2-C7-Br2 torsion angle is 13.3°; therefore, 4 may be viewed as a 3.7 Å spacer molecule. The structure of 1 shows the molecule has approximately twofold symmetry and includes one chloroform molecule, which is statistically disordered over two positions. The Br . . . Br distance is 3.90 Å and the Br atoms are pointing away from each other. The repulsion of the facing terminal thiophene rings, and especially between the bromine atoms, causes a relatively large interplanar angle between the terminal thiophene rings, 180−125.9= 54.1°. This is similar to the 58.5° for the interplanar angle between the terminal benzene rings in [6] helicene [K. P. Meurer, F. Vogtle, Top. Curr. Chem. 1985, 1–76; I. Navaza, G. Tsoucaris, G. LeBas, A. Navaza, C. deRango, Bull. Soc. Chim. Belg. 1979, 88, 863–870]. The individual thiophene rings are approximately planar with mean deviations of the least-square planes between 0.01 and 0.04 A; the angles between the least-square planes of neighboring thiophene rings are between 7.9 and 11.2°. With 35 the middle thiophene rings as a reference, the inner (C2, C3, C5, C7, C9, C11, C13, C15) helix climbs 2.92 Å and turns in-plane by 260°. Analogous values for [6] helicene are 3.12 Å and 317.7°, respectively. In both 1 and [6] helicene, the helix climbs for individual thiophene and benzene rings have similar patterns, with the smallest steps for the internal rings.

The above-noted synthetic route can be applied to the synthesis of higher homologues of 1. However, as the tetrafunctionalized module 1 is chiral, it would be more efficient to use a single enantiomer of 1 rather than its racemate as the starting material.

In the oligothiophenes of the formula (1) above and the intermediate compounds (4), (5) and (6) shown in the synthetic scheme set forth above, X may be bromine or iodine and Y is H or $SiR_1$ wherein $R_1$ is trialkyl with the alkyl group having from 1 to 6 carbon atoms. In the working examples set forth hereinafter, $R_1$ is either trimethyl or tri n-propyl, but compounds in which $R_1$ is constituted by other trialkyl groups having from 1 to 6 carbon atoms are also within the scope of the invention.

The following examples illustrate the practice of the invention.

EXAMPLE 1

General procedures and materials. Ether and tetrahydrofuran (THF) for use on vacuum line were freshly distilled from sodium/benzophenone prior to use Bis(phenylsulfonyl) sulfide was obtained according to the literature procedure: F. de Jong, M. J. Janssen J. Org. Chem. 1971, 36, 1645–1648. 4,4'-Dibromo-3,3'-dithienyl was obtained from 3,4-dibromothiophene following the method of Gronovitz (yield 40%, lit. yield 52%, S. Gronovitz, Acta Chem. Scand. 1961, 15, 1393–1395). $ZnCl_2$ (99.999%, ultra dry) was obtained from Alfa (johnson-Mathey). tBuLi (pentane) and nBuLi (hexane) were obtained from either Alrich or Acros; prior to use, their concentrations were determined by titration with N-pivaloyl-o-toluidine (J. Suffert J. Org. Chem. 1989, 54, 509–510). All other commercially available chemicals, including MeOD (99.5+%D), were obtained from Aldrich. Column chromatography was carried out on TLC grade silica gel (Aldrich), using 0–20 psig pressure. Preparative TLC (PTLC) was carried out using Analtech silica plates (tapered with a preadsorbent zone). Standard techniques for synthesis under inert atmosphere, using Schlenk glassware and gloveboxes (Mbraun and Vacuum Atmospheres), were employed.

NMR spectra were obtained using Bruker and Omega spectrometers ($^1H$, 500 MHZ and 300 MHZ) using $CDCl_3$ or benzene-$d_6$ ($C_6D_6$) as solvent. The chemical shift references were as follows: ($^1H$) TMS, 0.0 ppm ($CDCl_3$); benzene-$d_5$, 7.15 ppm; ($^{13}C$) $CDCl_3$, 77.0 ppm ($CDCl_3$); benzene-$d_6$, 128.4 ppm (benzene-$d_6$). Typical 1D FID was subjected to exponential multiplication with an exponent of 0.1 Hz (for $^1H$) and 1.0–2.0 Hz (for $^{13}C$).

IR spectra were obtained using a Nicolet Avatar 360 FT-IR instrument, equipped with an ATR sampling accessory (Spectra Tech, Inc.). A few drops of the compound in $CH_2Cl_2$ were applied to the surface of a ZnSe ATR plate horizontal parallelogram (45°, Wilmad). After the solvent evaporated, the spectrum was acquired (16 scans, 1 -cm$^-$1resolution).

GC/MS analyses were carried out using a Hewlet-Packard 5890/5972 instrument equipped with a 30m ×0.25 mm DB-5 capilary column. Typical oven temperatures were stepped up from 100 to 280° C. at a rate of 2°° C/min.

UV/Vis spectra were obtained on Hewlett-Packard (HP 8450A and HP8452A) diode array spectrophotometers.

MS analyses were carried out at the Midwest/Nebraska Center for Mass Spectrometry. Elemental analyses were carried out by M-H-W Laboratories, P.O. Box 15149, Phoenix, Ariz. 85060.

4,4'-dibromo-5,5-di(trimethylsilyl)-3,3'-dithienyl(3). nBuLi (1.94 M in hexane, 8.38 mL, 16.26 mmol, 2.2 equiv) was added dropwise to diisopropylamine (2.48 mL, 17.70 mmol, 2.4 equiv) in ether (35 mL) at 0° C. After 1.5 h at 0° C, 4,4'-dibromo-3,3'-dithienyl (2.394 g, 7.39 mmol) in ether (55 mL) was added dropwise. A large amount of a light yellow precipitate was formed.

The reaction mixture was stirred for 3 h at 0° C., and then chlorotrimethylsilane (4.69 mL, 36.95 mmol, 5.0 equiv) was added drop by drop at −78° C. After 3 h at −78° C., the reaction mixture was allowed to warm to ambient temperature overnight. After extraction with ether (200 mL), the combined organic layers was washed with water (3×150 mL) and then dried over MgSO$_4$. Concentration in vacuo gave a light yellow solid. Purification by flash chromatography (silica, hexane) yielded the product as a white solid (2.416 g, 70%). From two reactions on the 4 g and 8 g scales, 12.14 g (70.5%) of 3 was obtained from 11.92 g of 4,4'-dibromo-3,3'-dithienyl. A sample for NMR and MS was obtained by additional treatment with CHCl$_3$/CH$_3$OH (10:1, v/v). M.p. 92–92.5° C. $^1$H NMR (500 MHz, CDCl$_3$): δ+7.531 (s, 2H), 0.443 (s, 18H). $^3$C{$^1$H} NMR (500 MHz, CDCl$_3$): δ=138.0, 134.9,129.7, 119.6, –0.8 [J($^{29}$Si-$^{13}$C) =54 Hz]. IR (cm$^{-1}$): 3098.8, 2954.9, 2896.7(C-H). El-MS cluster: m/z (%RA for m/z -100 -1200): 471.9 ([M+6]$^{+,}$ 6%), 470.9 ([M+5]$^{+,}$ 10%), 469.9 ([M+4]$^{+,}$ 41%), 468.9 ([m+3]$^{+,}$ 17%), 467.9 ([M+2]$^{+,}$ 67%), 466.9 ([M+1]$^{+,}$ 465.9 (M $^{+,}$ 31%), 456.9 ([M+6-CH$_3$]$^+$, 9%), 455.9 ([M+5-CH$_3$+, 15%), 454.9 ([M+4-CH$_3$+, 62%), 453.9 ([M+3-CH$_3$]+, 25%), 452.9 ([M+2-CH$_{3]+,}$ 100%), 451.9 ([M+1-CH$_{3]+,}$ 12%), 450.9 ([M-CH$_3$]$^+$, 47%).

4,4'dibromo-5,5'-di(trimethylsilyl)-dithieno[2,3-b:3', 2'-dethiophone (4). nBuLi (1.94 M in hexane, 2.62 mL, 5.08 mmol, 2.3 equiv) was added dropwise to diisopropylamine (0.78 mL, 5.57 mmol, 2.5 equiv) in 190 mL dry ether at 0C. After 1 h at 0° C., 4,4'-dibromo-5,5'-di(trimethylsilyl)-3,3'-dithienyl (1.037 g, 2.21 mmol) in ether (8 mL) was added drop by drop. The reaction mixture was stirred for 2 h at 0° C., and then solid bis(phenylsulfonyl) sulfide (0.696 g, 2.21 mmol, 1.0 equiv) was added at −78° C. The reaction mixture was kept at −78° C. for 3 h, and then allowed to warm to ambient temperature overnight. The light yellow reaction mixture was washed with water (3x100 mL) and then dried over MgSO$_4$. Concentration in vacuo gave a yellow solid, which was purified by flash chromatography (silica, hexane) to give a white solid (0.805 g, 73%). From three reactions on the I g scale, 2.06 g (65%) of 4 was obtained from 3.0 g of 4,4'-dibromo-5,5'-di(trimethylsilyl)-3,3'-dithienyl. A sample for elemental analysis was obtained by recrystallization from chloroform/methanol (2:1, v/v) and then methanol/methylene chloride (1:1, v/v). A single crystal sample for x-ray crystallography was obtained from acetone. M.p. 153.5-154° C. Anal. Calcd. For C$_{14}$H$_{18}$S$_3$Si$_2$Br2: C, 33.73; H, 3.64. Found: C, 33.80; H, 3.69. H NMR (500 MHZ, C$_6$D6): δ=0.384 (s, J($^{13}$C-$^1$H)=120 Hz). $^{13}$C{H} NMR (500 MHZ, C$_6$D$_6$):δ=145.8, 139.4,138.6, 110.1,–0.4 [J($^{29}$Si-$^{13}$C)=55 Hz]. IR (cm$^{-1}$): 2953.2, 2895.6 (C-H). El-MS cluster: m/z (%RA for m/z=100–700). Found: 501.9 ([M+ 6]+, 17%), 500.9 ([M+5]+, 24%), 499.9 ([M+4]+, 82%), 498.9 ([M+3]+, 39%), 497.9 ([M+2]+, 100%), 496.9 ([M+ 1]+, 18%), 495.9 (M+, 68%). Calcd. forC$_{14}$Hl$_8$S$_3$Si$_2$Br$_2$: 501.8 (12%), 500.8 (175), 499.8 (66%), 498.8 (28%), 497.8 (100%), 496.8 (13%), 495.9 (46%). Found: 486.9 ([M+6-CH+, 13%), 485.9 ([M+5-CHJ+, 18%), 484.9 ([M+4-CHJ+, 71 %), 483.9 ([M+3-CHJ+, 29%), 482.9 ([M+2-CHJ+, 93%), 481.9 ([M+1-CHJ+, 14%), 489.9 ([M-CHJ+, 52%). Calcd. for C$_{13}$H,$_5$S$_3$Si$_2$Br$_2$: 486.8 (12%), 485.8 (17%), 484.8 (65%), 483.8 (27%), 482.8 (100%), 481.8 (13%), 480.8 (46%).

4,4'-dibromo-5-trimethylsilyldithienol[2,3-b:3', 2'-]thiophene (5). Trifluoroacetic acid (2.0 mL) was added dropwise to a vigorously stirred solution of 4,4'-dibromo-5, 5'-di(trimethylsilyl)-dithieno[2,3-b:3', 2'-dthiophene (1.758 g, 36.3 mmol) in chloroform (100 mL). The reaction was monitored with the TLC (silica, hexane). After 5, which possessed an intermediate R$_f$ compared to 4 and 6, appeared as the major component of the reaction mixture (ca. 30 min), water (150 mL) was added to the reaction mixture. Following the usual aqueous workup with chloroform, the resultant white solid was purified by flash chromatography (silica, hexane) to give white crystals of 5 (0.871 g). The side product 4,4'-dibromo-dithieno[2,3-b:3', 2'-dlthiophene (0.177 g) was recycled with LDA and chlorotrimethylsilane and then combined with the unreacted starting material. The additional 0.338 g of 5 was obtained. The overall yield of 5 was 80%. From two reactions on the 0.5 g and 0.3 g scales, 0.417 g (58%, without recycling of 6 and 4) of 5 was obtained from 0.838 g of 4,4'-dibromo-5,5'-di(trimethylsilyl)-dithieno[2,3-b:3', 2'-dlthiophene. M.p. 146–147° C. H NMR (500 MHZ, CDCl$_3$): δ=7.306 (s, IH,J($^3$C-H)=193 Hz), 0.463 (s, 9H,J($^{13}$C-$^1$H)=120 Hz). $^3$C{$^1$H} NMR (500 MHZ, CDCl$_3$):=144.3, 141.1, 138.9, 138.5, 135.1, 125.5, 108.9, 102.5, -0.8(J($^{29}$Si-$^{13}$C) 55 Hz]. IR (cm$^1$): 3112.3, 3098.3, 2956.2, 2892.3 (C-H). El-MS cluster: m/z (%RA for m/z =100–700): 429.9 ([M+6]+, 15 10%), 428.9 ([M+5]+, 12%), 427.9 ([M+4]+, 62%), 427.0 ([M+3]+, 19%), 425.9 ([M+2]+, 100%), 424.9 ([M+1]+, 9%), 424.0 (M+, 46%), 414.9 ([M+6-CHJ+, 8%), 413.9 ([M+5-CHJ+, 9%), 412.9 ([M+4-CHJ+, 50%), 411.9 ([M+ 3-CHJ+, 15%, 410.9 ([M+2-CHJ+, 84%), 409.9 ([M+1-CHJ+, 7%), 408.9 ([M-CHJ+, 39%).

4,4'-dibromo-dithieno[2,3-b:3', 2'-d]thiophene (6). M.p. 181–182° C. Anal. Calcd. for C$_8$H$_2$S$_3$Br$_2$: C, 27.14; H, 0.57. Found: C, 27.00; H, 0.20. H NMR (500 MHz, CDCl$_3$): 6=7.33 (s, J($^3$C,-H)=193 Hz). {$^3$CH} NMR (500 MHz, CDCJ$_3$): 6=140.6, 135.7, 125.5, 102.4, IR (cm): 3113.6, 3094.6 (C-H). GC-MS (CI): m/z 355 [M+1]+.

Bis(dithieno[2,3-b:3', 2'dthlophene) (7). nBuLi (2.10 M in hexane, 0.22 mL, 0.47 mmol, 1.0 equiv) was added to a solution of 3,4-dibromo-2-trimethylsilyl-dithieno[2,3-b:3', 2'-d]thiophene (200 mg, 0.47 mmol) in ether (12 mL) at --78° C.

After the solution was stirred for 3 h at -78° C., CuCl$_2$ (629 mg, 10 equiv) was added. The reaction mixture was kept at --78° C. for another 3 h. Subsequently, the reaction mixture was allowed to warm to ambient temperature over several hours and then kept at ambient temperature for another 1–2 days. The usual aqueous workup gave 170 mg of a light yellow solid. The compound was purified by column chromatography (flash silica, hexane/benzene, 14:1, v/v), yielding 57.3 mg (35%) of 7 as a white powder. From two reactions on the 0.02 g and 0.4 g scales, 0.11 g (32%) of 7 was obtained from 0.42 g of 4,4'-dibromo-5-trimethylsilyl-dithieno[2,3-b:3'2'-d]thiophene. A sample for elemental analysis was obtained by recrystallization from chloroform/methanol (1:5, v/v). M.p. 260–261°C. Anal. Calcd. for C$_{22}$H$_{20}$S$_6$Si$_2$Br$_2$: C, 38.14; H, 2.91. Found: C,38.07; H, 3.16. H NMR (500 MHz, CDCl$_3$): 6=7.321 (s, 2H, J($^{13}$C-H)=189 Hz), 0.324 (s, 18H, J($^{13}$C-)=120 Hz). $^3$C{H} NMR (500 MHz, CDCl$_3$): δ=143.6, 140.4, 139.7, 138.3, 137.2,130.5,128.0, 109.1, -0.8[J($^{29}$Si-$^3$C)=55 Hz]. IR (cm$^{-1}$): 5 3109.1, 2951.3, 2892,0, 2850.3(C-H). HR EI-MS cluster: m/z (ion type, relative intensity in % for m/z =400–750, deviation for the formula): 693.7737 ([M+4]+, 42%, 2.4 ppm for $^{12}$C$_{22}$H$_{20}$S$_6$Si$_2$$^8$Br$_2$), 691.7755 ([M+2]+, 100%, 2.7 ppm for $^{12}$C22H$_{20}$S$_6$Si$_2$$^{79}$BrBr), 689.7786 (M+, 80%, 1.2 ppm for $^{12}$C22H$_{20}$S$_6$Si$_2$$^{79}$Br$_2$).

Helicene (1). LDA (2.3 equiv) was added to 7 (56.2 mg, 0.081 mmol, 1 equiv) in ether (12 mL) at 0° C. After the solution was stirred at 0° C. for 2 h, dry bis(phenylsulfonyl) sulfide (28.1 mg, 0.089 mmol, 1.1 equiv) was added at −78° C. The solution was kept at −78° C. for 3h, then allowed to warm to ambient temperature over a 12 h period. The usual aqueous workup was followed by flash chromatography (silica gel) using hexane/chloroform (10:1, v/v). The 15 product was obtained as a powder, 27.8 mg (47%). From two reactions on the 0.01 g and 0.09 g scales, 43.5 mg (41%) of 1 was obtained from 102.4 mg of 7. Samples for elemental analysis and x-ray crystallography were obtained by recrystallization from chloroform/acetone (2:1, v/v). M.p. 311–312.5° C. Anal.

Calcd. for $C_{22}H_{28}S_7Si_2Br_2$: C, 36.56; H, 2.51. Found: C, 36.88; H, 2.89. H NMR 2(500 MHz, $CDC6_3$):=0.376 (s, J($^{13}$C-H)=120 Hz). $^{13}C\{H\}$ NMR (500 MHz, $CDCI_3$):δ= 143.4, 140.6, 140.4, 139.4, 135.9, 131.8, 130.3, 112.5, -0.7[J($^{29}$Si-$^{13}$C) =54 Hz]. IR (cm-): 2953.6, 2922.6, 2897.7, 2851.3 (C-H). HR El-MS cluster: m/z (ion type, relative intensity in 5 for m/z =100–125, deviation for the formula): 723.7336 ([M+4]+, 68%, -2.5 ppm for $^{12}C_{22}H_8S_7Si_2{}^{8}Br_2$), 721.733825 ([M+2]+, 100%, 0.0 ppm for $^{12}C_{22}H_8S_7Si_2{}^{79}Br^1$ Br), 719.7378 (M+, 26%, -2.6 ppm for $^{12}C_{22}H_8S_7Si_2{}^{79}Br_2$)

4,4'dibromo-5,5'di(tri-n-propylsilyi)-dithieno[2,3-b:3', 21-dthlophene (8). nBuLi (2.53 M in hexane, 0.26 mL, 0.66 mol, 2.3 equiv) was added dropwise to diisopropylamine (0.093 mL, 2.5 equiv) in ether (30 mL) at 0° C. After 1.5 h at 0° C, crystalline 4,4'-dibromo-dithieno[2,3-b:3', 2'-d] thiophene (0.100 g, 0.28 mmol) was added. Light yellow mixture with some precipitate was stirred for 3.5 h at 0° C., and then chlorotri-n-propylsilane (0.31 mL, 1.41 mmol, 5.0 equiv) was added drop by drop at −78° C. After 3 h at −78° C., the reaction mixture was allowed to warm to ambient temperature overnight. After the usual aqueous workup with ether, column chromatography (silica, hexane) and crystallization (chloroform/methanol, 2:1) yielded 94.0 mg (315) of 8 as a white powder. M.p. 141–142° C. H NMR (500 MHz, $CDCI_3$):δ=1.45–1.36 (m, 12H), 1.02–0.94 (m, 30H). $^{13}C\{H\}$NMR(500 MHz, $CDCI_3$):δ=145.1,138.2,136.6, 109.1,18.4, 17.5,15.2 Uj($^{29}$Si-$^{13}$C) [55 Hz]. HR El-MS cluster: m/z (ion type, relative intensity in % for mlz - 480–608, deviation for the formula): 668.0344 ([M+4]+, 70%, -4.7 ppm for $^{12}C_{26}H_{42}S_3Si_2$ Br2), 666.0363 ([M+2]+, 100%, -4.4 ppm for $^{12}C_{26}H_{42}S_3Si_2{}^{79}Br8Br$), 664.0351 (M+, 43 %, 0.5 PPM FOR $1^2C_{26}H_{42}S_3Si_2{}^{79}Br_2$).

In view of the above, it will be seen that the several objects of the invention are achieved and other advantageous results attained.

As various changes could be made in the above compositions and processes, without departing from the scope of the invention, it is intended that all matter contained in the above description shall be interpreted as illustrative and not in a limiting sense.

What is claimed is:

1. A compound of the formula:

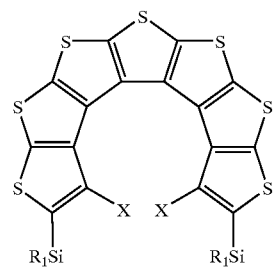

wherein X is Br or I and $R_1$ is trialkyl with the alkyl group having from 1 to 6 carbon atoms.

2. A compound as set forth in claim 1 wherein $R_1$ is trimethyl.

3. A compound as set forth in claim 1 wherein X is Br.

4. A compound as set forth in claim 1 wherein $R_1$ is trimethyl and X is Br.

5. A compound as set forth in claim 1 wherein $R_1$ is the tri-n-propyl.

6. A compound of the formula:

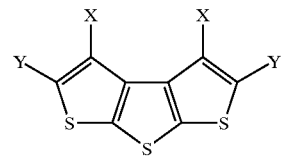

wherein X is Br or I and Y is H or SiR, wherein $R_1$ is trialkyl with the alkyl group having from 1 to 6 carbon atoms.

7. A compound as set forth in claim 6 wherein $R_1$ is trimethyl.

8. A compound as set forth in claim 6 wherein X is Br.

9. A compound as set forth in claim 6 wherein $R_1$ is trimethyl and X is Br.

10. A compound as set forth in claim 6 wherein $R_1$ is tri-n-propyl.

11. A process for preparing compounds of the formula:

(1)

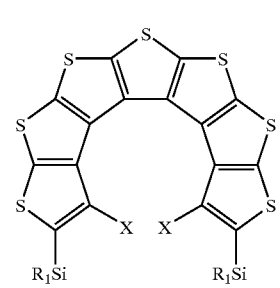

wherein X is Br or I and $R_1$ is trialkyl with the alkyl group having from 1 to 6 carbon atoms, said process comprising the steps of (a) converting a compound of the formula:

(2)

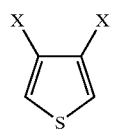

wherein X is Br or I, to a compound of the formula:

(3)

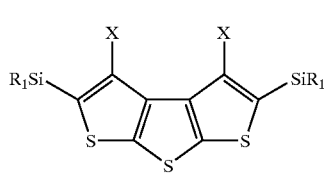

wherein X is as defined above and $R_1$ is trialkyl with the alkyl group having from I to 6 carbon atoms;

(b) cross-conjugating compounds of the formula (3) above to a compound of the formula:

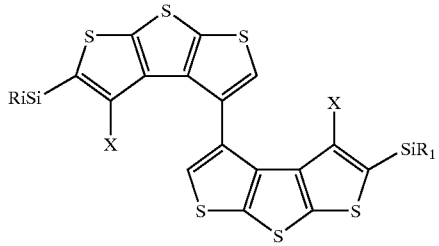 (4)

wherein X and R₁ are as defined above; and (c) annelating a compound of the formula (4) above to produce an oligothiophene helix of the formula (1) above.

12. A process as set forth in claim 11 wherein $R_1$ in compound (1) is trimethyl.

13. A process as set forth in claim 11 wherein X in compound (1) is Br.

14. A process as set forth in claim 11 wherein $R_1$ is trimethyl and X is Br.

15. A process as set forth in claim 11 wherein $R_1$ is tri-n-propyl.

* * * * *